United States Patent
Mosler et al.

(10) Patent No.: US 7,458,964 B2
(45) Date of Patent: Dec. 2, 2008

(54) CATHETER MOVEMENT CONTROL DEVICE

(75) Inventors: Theodore J. Mosler, Raleigh, NC (US);
Todd M. Korogi, Raleigh, NC (US);
Scott P. Jarnagin, Raleigh, NC (US); **F.
Peter Hiltz, Raleigh, NC (US); John H.
Golden**, Atlanta, GA (US)

(73) Assignee: Medical Technologies of Georgia, Inc.,
Covington, GA (US)

( * ) Notice: Subject to any disclaimer, the term of this patent is extended or adjusted under 35 U.S.C. 154(b) by 162 days.

(21) Appl. No.: 11/555,307

(22) Filed: Nov. 1, 2006

(65) Prior Publication Data

US 2008/0103464 A1  May 1, 2008

(51) Int. Cl.
*A61M 5/178* (2006.01)
*A61M 5/00* (2006.01)
*F16K 7/04* (2006.01)

(52) U.S. Cl. .............. 604/540; 604/159; 604/171; 604/172; 604/164.07; 251/4

(58) Field of Classification Search ............... 604/528, 604/171, 172, 164.07, 165.01, 159, 540, 604/328; 251/4–9
See application file for complete search history.

(56) References Cited

U.S. PATENT DOCUMENTS

| | | | |
|---|---|---|---|
| 3,854,483 A | 12/1974 | Powers | 128/349 |
| 4,062,363 A | 12/1977 | Bonner, Jr. | 128/349 |
| 4,621,842 A | 11/1986 | Kowal et al. | |
| 4,722,560 A | 2/1988 | Guest | |
| 4,773,198 A * | 9/1988 | Reinhardt | 52/223.13 |
| 5,147,341 A | 9/1992 | Starke et al. | 604/349 |
| 5,226,530 A | 7/1993 | Golden | 206/210 |
| 5,584,513 A | 12/1996 | Sweeny et al. | |
| 6,004,305 A | 12/1999 | Hursman et al. | 604/328 |
| 6,053,905 A | 4/2000 | Daignault, Jr. et al. | 604/544 |
| 6,391,010 B1 * | 5/2002 | Wilcox | 604/328 |
| 6,402,726 B1 | 6/2002 | Genese | |
| 6,602,224 B1 | 8/2003 | Simhambhatla | 604/96.01 |
| 6,638,269 B2 * | 10/2003 | Wilcox | 604/528 |
| D483,869 S * | 12/2003 | Tran et al. | D24/129 |

FOREIGN PATENT DOCUMENTS

WO    WO 02/074206 A1 *    9/2002

* cited by examiner

*Primary Examiner*—Tatyana Zalukaeva
*Assistant Examiner*—Michael G Bogart
(74) *Attorney, Agent, or Firm*—Ballard Spahr Andrews & Ingersoll, LLP

(57) ABSTRACT

The present invention relates to a device for controlling movement of a catheter that is at least partially disposed therein a urinary catheter pouch. The invention particularly relates to a catheter movement control device for use with a urinary catheter pouch which aids in preventing the catheter from moving back into the pouch once the catheter has been deployed. The device makes it easier to use a urinary catheter contained in a urinary catheter pouch. This is especially true for those with disabilities that would have difficulty gripping the catheter within the pouch.

13 Claims, 7 Drawing Sheets

CATHETER MOVEMENT CONTROL DEVICE

BACKGROUND OF THE INVENTION

1. Field of the invention

The present invention relates to a device for preventing a urinary catheter from retracting back into a urinary catheter pouch during use. Particularly, the invention relates to a device that allows the user of a urinary catheter, which is contained within a sterile urinary catheter pouch, to advance the catheter out of the pouch and towards the user while a movement control device prevents the catheter from retracting back into the pouch after such advancement.

2. Description of the Related Art

A wide variety of catheters are available for insertion into the body for introduction or withdrawal of fluids. Urinary catheters are flexible tubes designed to drain urine from the bladder by insertion into the urethra. They are packaged in sterile containers and can be lubricated for insertion prior to packaging or prior to use. Intermittent urinary catheters are designed to be inserted for each use and are commonly used by patients who are able to catheterize themselves. One type of intermittent catheter comprises a urine catheter pouch, which also serves as the sterile package for the catheter. See, for example, U.S. Pat. No. 3,854,483 to Powers, U.S. Pat. No. 5,226,530 to Golden, U.S. Pat. No. 6,004,305 to Hursman et al, U.S. Pat. No. 5,147,341 to Starke et al and U.S. Pat. No. 6,053,905 to Daignault et al. Another type of catheter is an intermittent catheter contained in a conduit pouch, whereby the pouch can be opened and used to transfer urine to the toilet or a urine collection container.

Catheterization is accomplished by introducing the proximal tip of a catheter into the urethra, and then "longitudinally collapsing and extending the pouch in an accordion-like manner until the tip reaches the bladder" as described in U.S. Pat. No. 6,602,224 to Kavanagh and U.S. Pat. No. 4,062,363 to Bonner. The portion of the catheter remaining within the pouch is gripped between the walls of the pouch advanced out of the pouch and into the urethra. During the pouch-extending phase, the catheter is held to resist a movement of the catheter back into the pouch by gripping the catheter between the pouch walls. The operation requires two hands to accomplish, as well as dexterity to make sure that the catheter does not retract back into the pouch. It is a difficult, if not impossible, activity for a quadriplegic, high paraplegic or person with low grip strength or dexterity to accomplish. Few, if any, products serve the self catheterization market for these users.

Further, complications can make the process next to impossible, even for those with great dexterity or strength. For example, the fluid pressure from the bladder or the weight from the urine may tend to pull the lubricated catheter from the urethra and back into the urinary catheter pouch. To prevent this from occurring, the user must continuously grip the catheter until voiding is completed. Catheters are normally heavily lubricated and have to be gripped between the walls of the plastic pouch. This can create a "slippery noodle" effect, which means that the grip strength and dexterity required to immobilize the catheter from retracting into the pouch may be so great that self-catheterization becomes impossible, even for someone with normal grip strength or dexterity.

Accordingly, it would be useful to have a catheter movement control device that is easy to manufacture and provides the user with a viable option to assist in the routine of self-catheterization.

SUMMARY OF THE INVENTION

The present invention provides a device for controlling movement of a catheter that is at least partially disposed therein a urinary catheter pouch. The invention particularly relates to a catheter movement control device for use with a urinary catheter pouch which aids in preventing the catheter from moving back into the pouch once the catheter has been deployed. The device makes it easier to use a urinary catheter contained in a urinary catheter pouch. This is especially true for those with disabilities that would have difficulty gripping the catheter within the pouch.

The catheter movement control device comprises a catheter housing defining a longitudinally extending catheter tube pathway configured for receipt of the catheter. In one aspect, the catheter movement control device can selectively engage the catheter to permit longitudinal movement of the catheter relative to the catheter tube pathway in a first direction and to resist longitudinal movement of the catheter relative to the catheter tube pathway in a second, opposite direction.

In one aspect, the catheter tube pathway has an egress end and an ingress end. The egress end is positioned external of a urinary catheter pouch and the ingress end is contained within an interior volume of the urinary catheter pouch. As such, in one aspect, the first direction mentioned above is the longitudinal direction extending toward the egress end of the housing from the ingress end of the housing.

These and other objects of the present invention will be clear when taken in view of the detailed specification and disclosure in conjunction with the appended figures.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 2b is a cross-sectional view of an alternate embodiment of the catheter movement control device of FIG. 2a.

DETAILED DESCRIPTION OF THE INVENTION

Figure 1A:
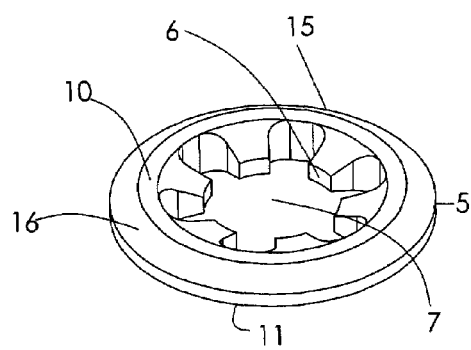
FIGS. 1a, 1b, 1c, 1d, 1e, and 1f are perspective views of a tube gripper of the invention with various numbers of gripping surfaces.
Figure 1B:
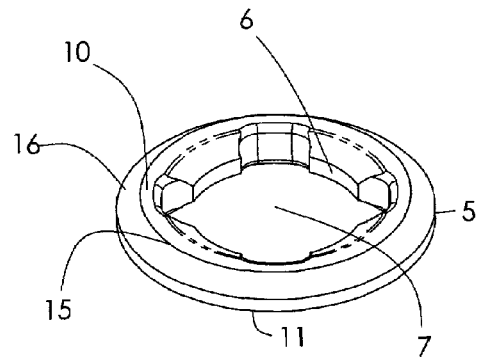
Figure 1C:
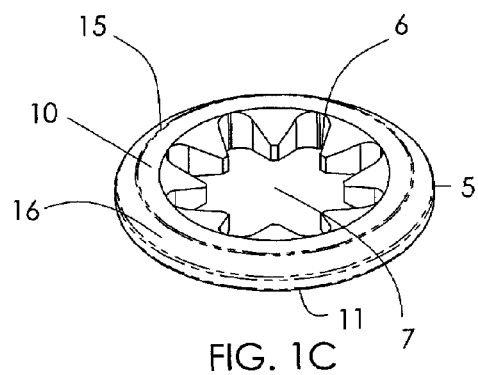
Figure 1D:
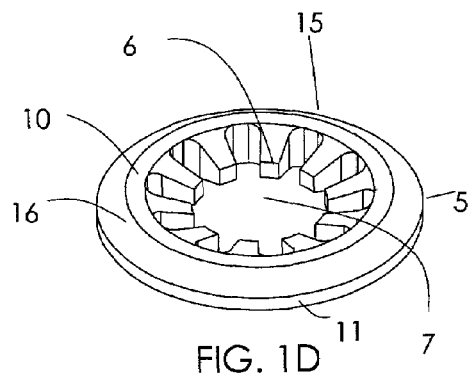
Figure 1E:
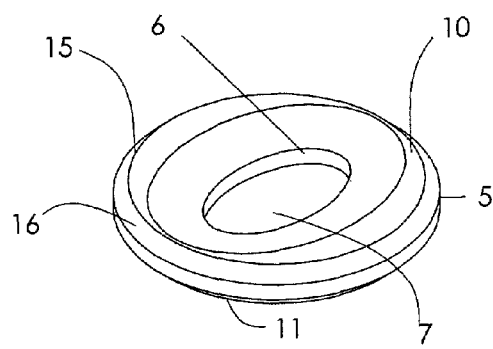
Figure 1F:
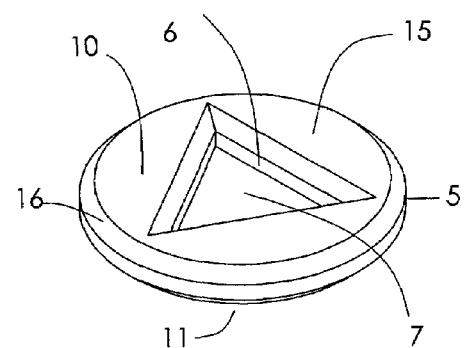

The present invention may be understood more readily by reference to the following detailed description of the invention and the Examples included therein and to the Figures and their previous and following description.

Before the present systems, articles, devices, and/or methods are disclosed and described, it is to be understood that this invention is not limited to specific systems, specific devices, or to particular methodology, as such may, of course, vary. It is also to be understood that the terminology used herein is for the purpose of describing particular embodiments only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used in the specification and the appended claims, the singular forms "a," "an" and "the" include plural referents unless the context clearly dictates otherwise. Thus, for example, reference to "a catheter movement control device" includes two or more such devices, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

The present invention relates to a device for controlling movement of a catheter 50 that is at least partially disposed therein a urinary catheter pouch. The invention particularly relates to a catheter movement control device for use with a urinary catheter pouch which aids in preventing the catheter from moving back into the pouch once the catheter has been deployed. The device makes it easier to use a urinary catheter contained in a urinary catheter pouch. This is especially true for those with disabilities that would have difficulty gripping the catheter within the pouch.

The catheter movement control device 1 comprises a catheter housing 60 defining a longitudinally extending catheter tube pathway 61 configured for receipt of the catheter 50. In one aspect, the catheter movement control device 1 can selectively engage the catheter to permit longitudinal movement of the catheter relative to the catheter tube pathway 61 in a first direction and to resist longitudinal movement of the catheter 50 relative to the catheter tube pathway in a second, opposite direction.

In one aspect, the catheter housing 60 is a rigid or semi-rigid structure which defines the catheter tube pathway 61. The housing can be made of virtually any material normally used inside urinary catheter pouches, but in general, the housing would be a rigid or semi rigid polymer such as polypropylene, polyethylene, polycarbonate, or the like. The catheter tube pathway inside the catheter housing 60 would be large enough to allow free movement of a catheter longitudinally, but small enough that it prevents a great deal of movement laterally. In one aspect, there is no more than about 2-3 millimeters of play between the catheter tube and the walls of the catheter tube pathway.

In one aspect, the catheter tube pathway has an egress end 41 and an ingress end 40. The egress end 41 is positioned external of a urinary catheter pouch and the ingress end 40 is contained within an interior volume of the urinary catheter pouch. As such, in one aspect, the first direction mentioned above is the longitudinal direction extending toward the egress end 41 of the housing from the ingress end 40 of the housing.

In another aspect, as a way for engaging the catheter, the catheter movement control device also comprises a leveling surface 30, a biasing surface 31, and a tube gripper 5. The leveling surface 30 is positioned within the catheter tube pathway of the housing, proximate the egress end of the catheter tube pathway 61. In this aspect, the leveling surface is positioned substantially normal to the longitudinal axis of the housing. The biasing surface 31 is positioned within the catheter tube pathway of the housing at an acute angle with respect to the leveling surface. The biasing surface may be a solid surface that is angled, or it may also be a plurality of uneven surfaces. The biasing surface may also be a single level surface that only partially surrounds the catheter pathway. This biasing surface is spaced from the leveling surface and, consequently, the biasing surface and leveling surfaces define an interior cavity within the catheter tube pathway of the housing. In one aspect, the leveling surface 30 and the biasing surface 31 are spaced a distance approximately equal to, or greater than, the thickness of the tube gripper 5.

In yet another aspect, the tube gripper 5 is positioned within the interior cavity of the housing. The tube gripper has a top face 10, a bottom face, and defines a catheter orifice extending between the top face 10 and the bottom face. In one aspect, the catheter orifice comprises a gripping surface 6 configured to frictionally engage an exterior surface of the catheter.

In another aspect, the tube gripper 5 is configured to move about and between a first position and a second position. In the first position, at least a portion the top face of the tube gripper is in contact with the leveling surface, such that the catheter orifice of the tube gripper is positioned substantially co-axial to the axis of the catheter tube pathway. In the second position, at least a portion of the bottom face of the tube gripper is in contact with the biasing surface such that the catheter orifice is positioned at an acute angle with respect to the axis of the catheter tube pathway 61. In one aspect, the tube gripper 5 is configured such that, upon the application of an external force on the catheter 50 resulting in longitudinal movement of the catheter 50 in the first direction, the tube gripper is positioned in the first position adjacent the leveling surface. In another aspect, the tube gripper is configured such that, upon the application of an external force on the catheter resulting in longitudinal movement of the catheter in the second direction, the tube gripper is positioned in the second position adjacent the biasing surface. As such, in the first position, the catheter orifice is sized such that the gripping surface 6 of the tube gripper 5 provides a first level of resistance to the movement of the catheter relative to the catheter tube pathway, while in the second position, the gripping surface 6 of the tube gripper provides a second level of resistance to the movement of the catheter relative to the catheter tube pathway. In this aspect, the second level of resistance is greater than the first level of resistance. In other words, the first level of resistance, in one aspect, is enough to lightly grip the catheter tube such that the gripper is moved, along with the catheter, from the first position to the second position. As one skilled in the art will appreciate, the biasing of the tube gripper increases the friction between the gripping surface and the catheter tube.

As one skilled in the art will appreciate, the tube gripper 5 may be a variety of shapes. In one aspect, the tube gripper is substantially ring shaped. However, the gripper may be almost any shape, such as, but not limited to, oval, triangular, square, and the like. Additionally, the gripper may be constructed of a rigid or semi-rigid material, although softer materials are also contemplated. Some examples of appropriate polymers for constructing the gripper include, but are not limited to, polypropylene, polyethylene, polycarbonate, and the like.

In another aspect, the gripping surface comprises a plurality of gripping surfaces 6, as can be seen in FIGS. 1a through 1f. The design of the gripping surfaces depends on a number of variables, such as, the material of the catheter, the material of the gripper, the size of the gripper, and so on. One skilled in the art will size the tube gripper accordingly, however, in one aspect, the tube gripper has a dimension 20 extending from the top face to the bottom face of from about 1 mm to about 3 mm. In yet another aspect, the tube gripper has chamfered edges 16. As illustrated in the figures, the gripping surfaces may comprise flat surfaces, points, edges, or other shapes known in the art.

As illustrated in the figures, in one aspect, the catheter housing comprises a catheter introducer tip 51. In another aspect, the leveling surface 30 is positioned within a portion of the catheter introducer tip 51.

FIGS. 1a, 1b, 1c, 1d, 1e and 1f depict angle perspectives of six embodiments of a tube gripper of the invention with variations on the gripping surface. Shown in each embodiment is the top face 10 with the bottom face 11 underneath, not visible in these views.

Figure 2A:
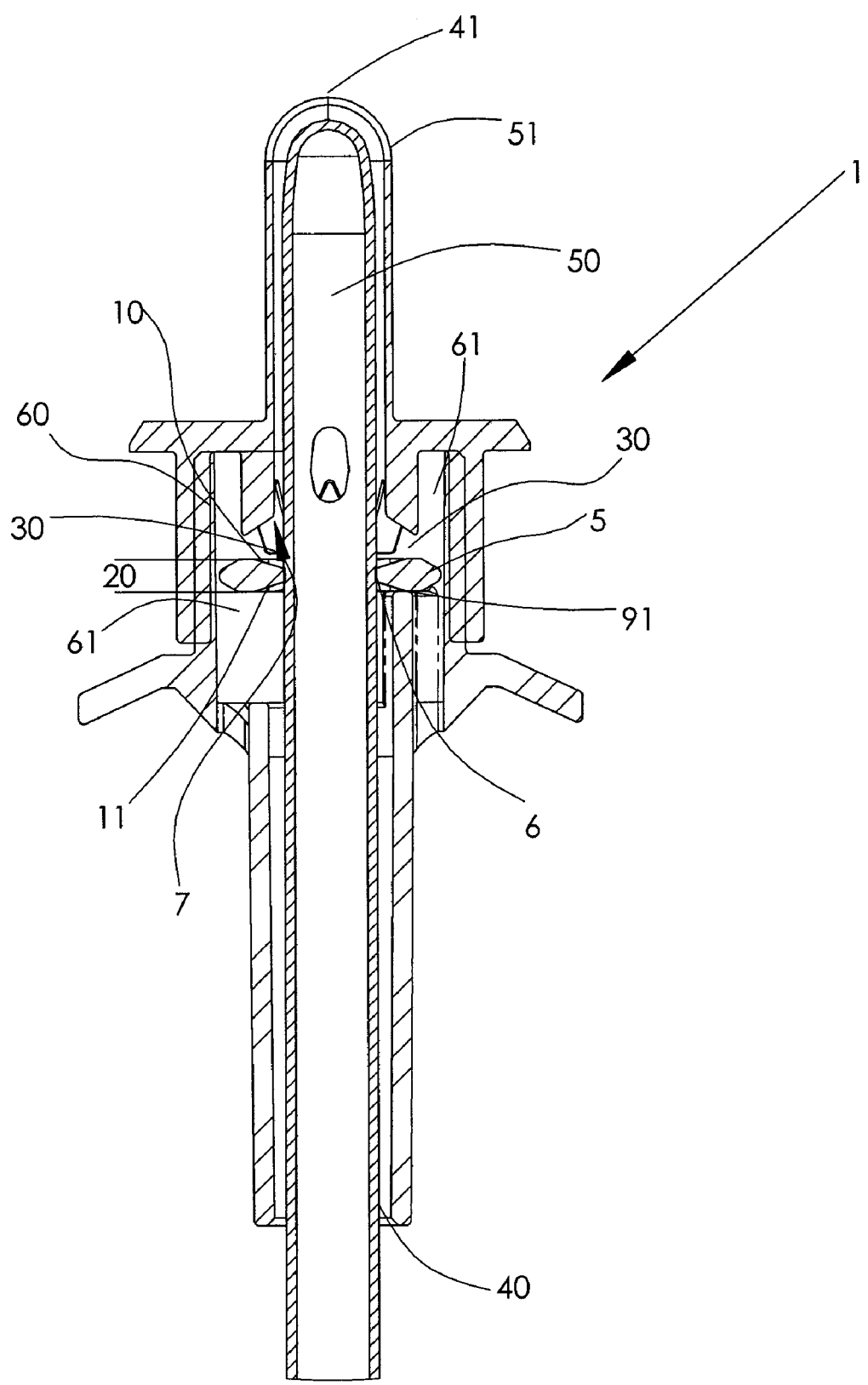
FIG. 2a is a cross-sectional view of an embodiment of the invention for a catheter movement control device, showing the tube gripper level against a leveling surface.
Figure 2B:
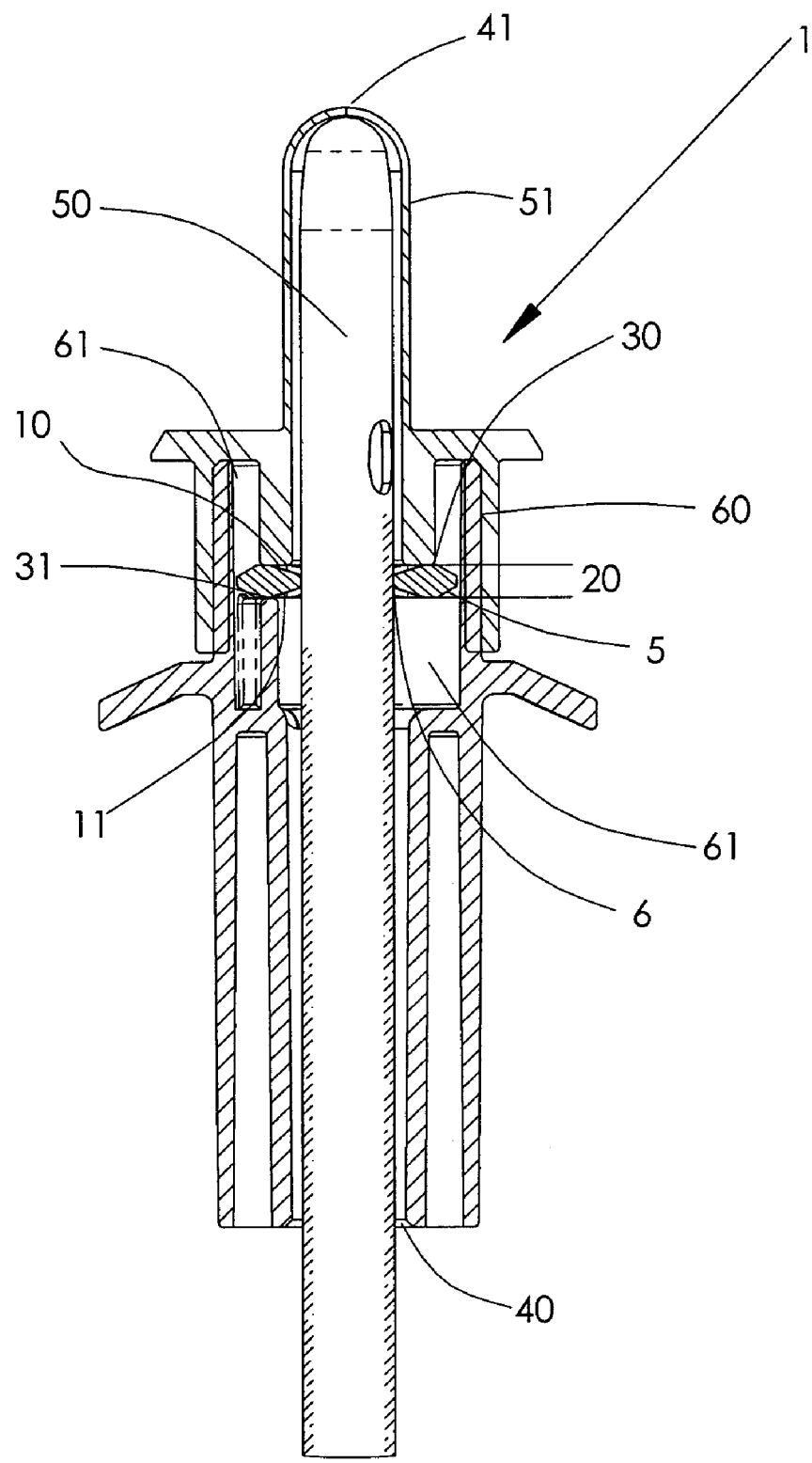

FIGS. 2a and 2b disclose alternate cross-sectional views of a catheter movement control device I of the invention. In these views, a cross-sectional view of a tube gripper 5 is shown. In these views, gripping surfaces 6 are barely touching the catheter 50, thus allowing the tube gripper 5 to move longitudinally in the first direction with movement of catheter 50 until the tube gripper 5 reaches the leveling surface 30. In view 2a, the catheter 50 is at rest and has neither moved in the ingress or first direction. In view 2b, the catheter 50 has moved slightly in the first direction and now the tube gripper 5 is touching the leveling surface 30, whereas in 2a, the tube gripper 5 has not yet touched the leveling surface. Views 2a and 2b also show different types of leveling surfaces. In view 2a, the leveling surface 30 is a series of level points positioned within a portion of a catheter introducer tip 51. In view 2b, the leveling surface 30 is a fixed circular shoulder. As can be seen, when the tube gripper 5 reaches the leveling surface 30, the tube gripper 5 is held normal to the catheter 50, thus lightly gripping the catheter 50 and not impeding the movement of catheter 50 in the first direction.

The cross-sectional view of the biasing surface 31 is seen in both FIGS. 2a and 2b, as well. In one aspect, the distance between the leveling surface 30 and the biasing surface 31 is approximately the thickness 20 of tube gripper 5. The tube gripper 5 does not substantially bias or tilt in this view because the catheter 50 has not moved in the second direction in these views. FIGS. 2a and 2b each show the catheter housing 60, which defines catheter tube pathway 61. A portion of the catheter 50 is positioned in the catheter tube pathway 61, as is the tube gripper 5, leveling surface 30 and biasing surface 31.

Figure 3A:
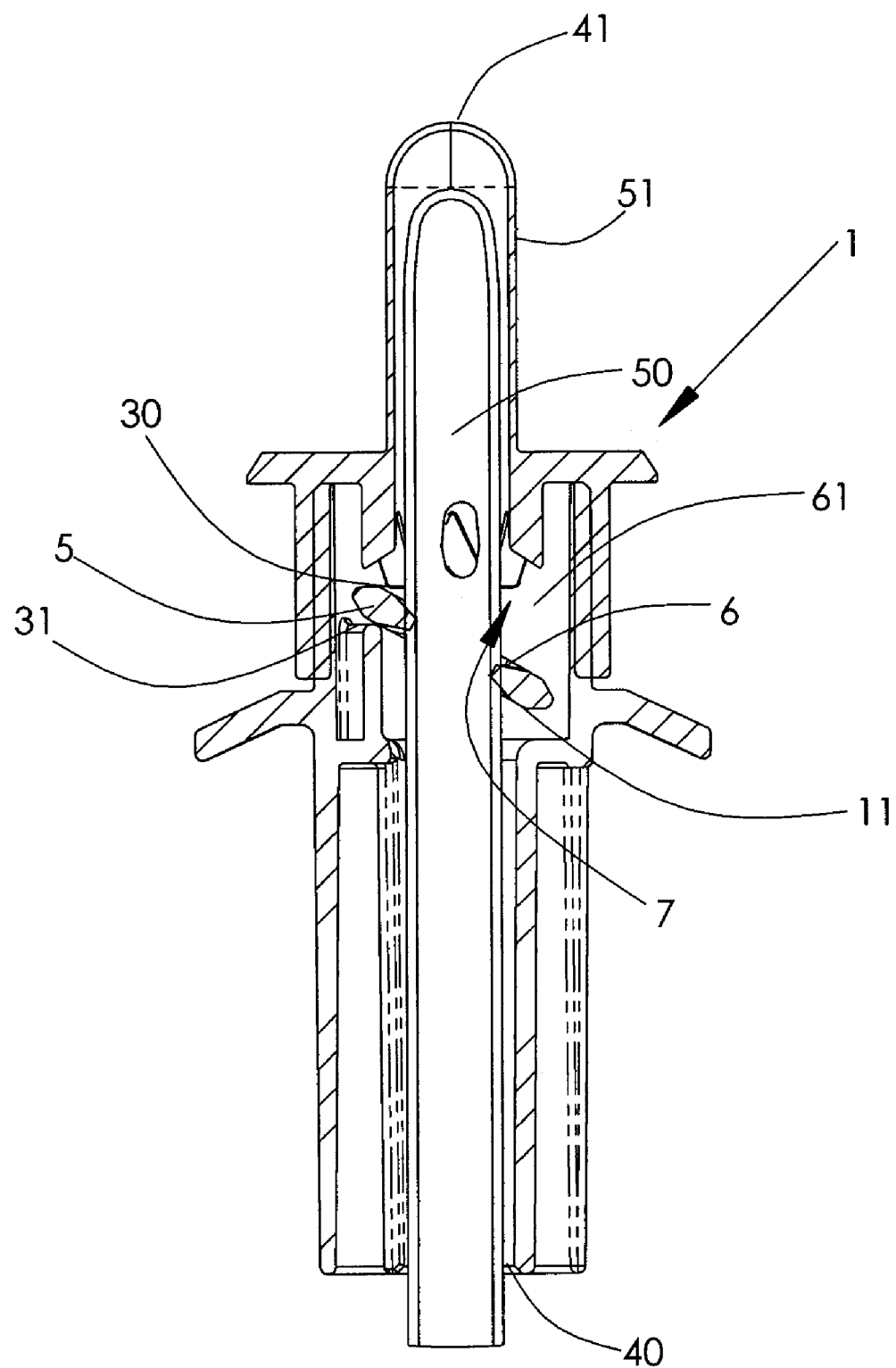
FIGS. 3a and 3b show a cross-sectional view of an embodiment of the catheter movement control device of FIG. 2a, showing the tube gripper biasing against the biasing surface.
Figure 3B:
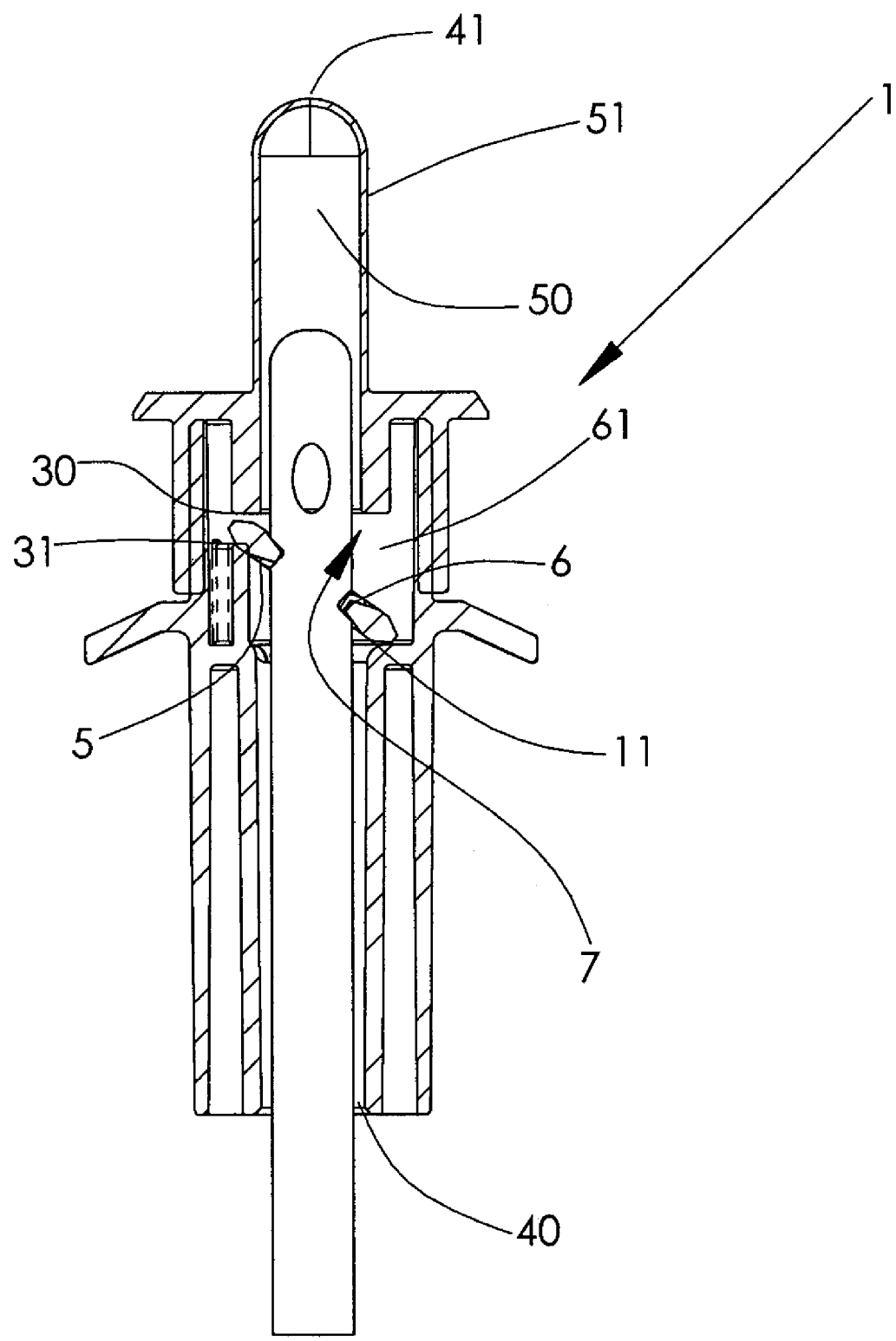

FIGS. 3a and 3b show a cross-sectional view of the movement control device 1, depicting the catheter 50 having been moved in the second direction. In these views, tube gripper 5 has moved in the second direction, along with the catheter 50, and has biased off of the biasing surface 31. In the view shown, the gripper 5 has biased about 45 degrees, but it only needs to bias enough to grip the catheter 50 in order to impede the catheter's movement in the second direction. As can be seen in these views, upon biasing, the tube gripper 5 gripping surfaces 6 grab the catheter 50. When the catheter 50 moves in the second direction, it takes the tube gripper with it as the tube gripper 5 lightly grabs the catheter 50. When the tube gripper 50 reaches the biasing surface 31, a portion of the bottom face of the tube gripper 5 that touches the biasing surface 31 can not proceed further while the opposite portion of the bottom face of the tube gripper 5 continues until it either meets an obstruction or, in the case of the aspects shown, the gripping surfaces 6 grab into the catheter 50 due to the relative narrowing of the catheter orifice 7. At this point, the catheter 50 is resisted from advancing in the second direction any further since the tube gripper has a grip on it.

Figure 4A:
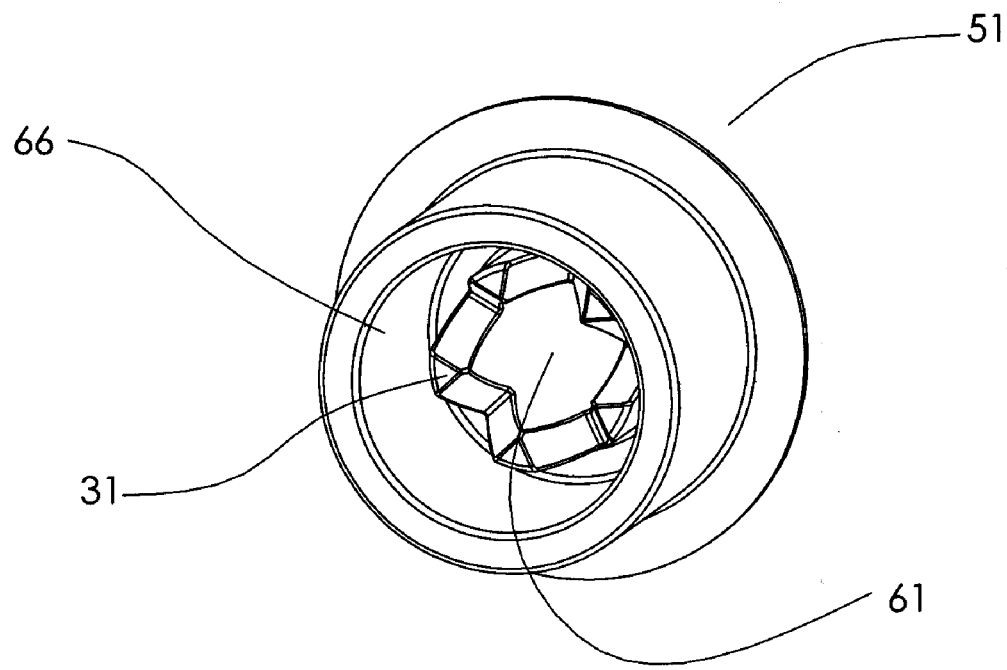
FIGS. 4a and 4b are top and bottom perspective views of an introducer tip with a leveling surface defined therein.
Figure 4B:
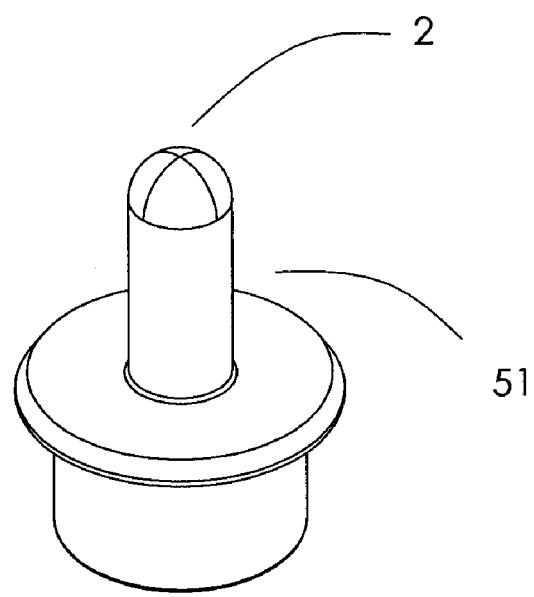

In FIGS. 4a and 4b, a catheter introducer tip 51 is shown. In FIG. 4a, the bottom view of the catheter introducer tip 51 shows that the leveling surface 30 is built into a portion of the catheter introducer tip 51. In this aspect, the introducer tip 51 defines the upper part of the housing 60, as well as a portion of the catheter tube pathway 61.

Figure 5:
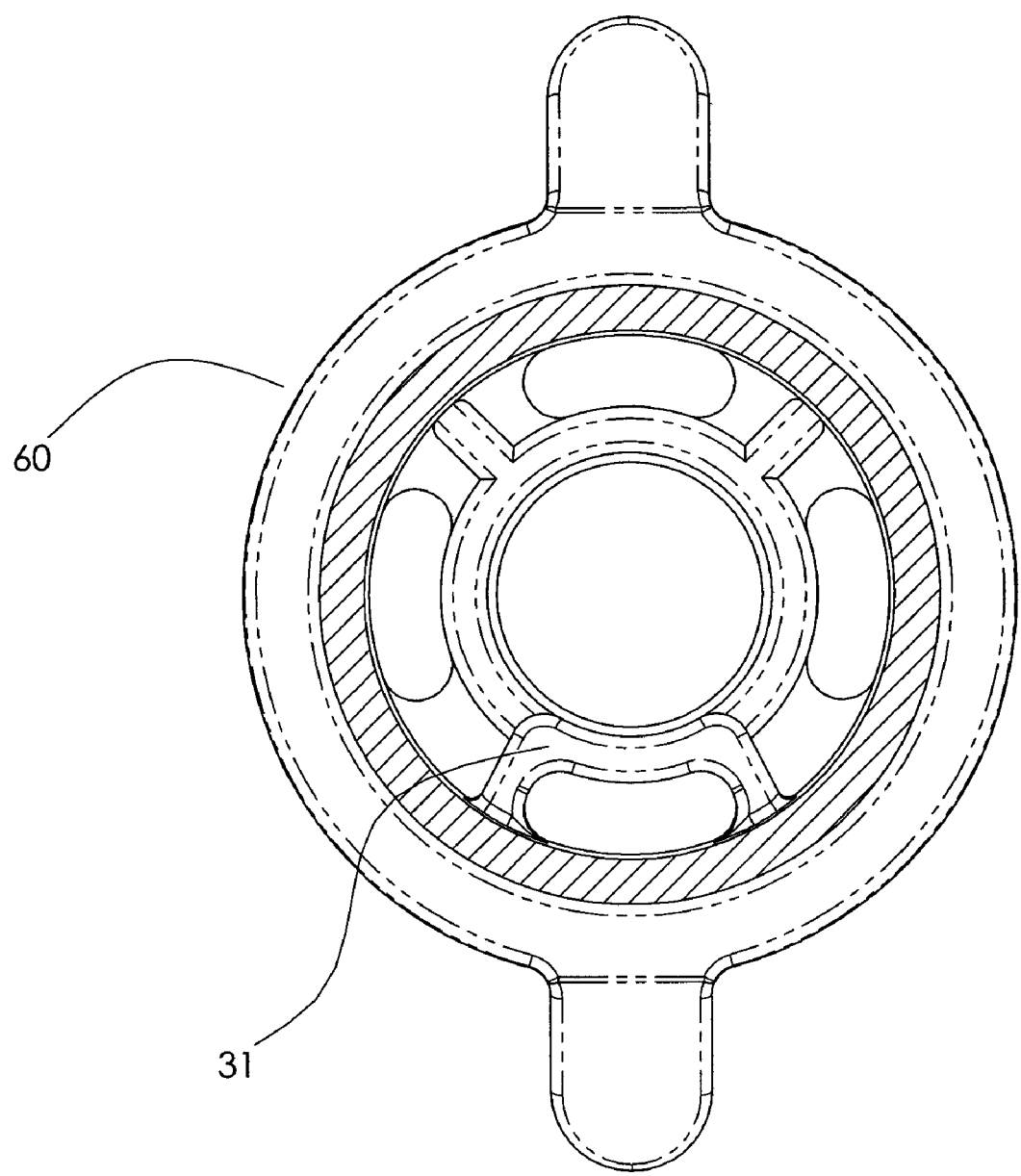
FIG. 5 is a top perspective cross-sectional view of a biasing surface within a catheter housing.

FIG. 5 depicts a cross-sectional view of the catheter housing 60, directly above the biasing surface 31. In this embodiment, the biasing surface occupies about one sixth of the circumference of the housing 60. As discussed above, a larger or smaller surface could be chosen by one skilled in the art.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims.

Moreover, although specific terms are employed herein, as well as in the claims which follow, they are used only in a generic and descriptive sense, and not for the purposes of limiting the described invention, nor the claims which follow.

What is claimed is:

1. A device for controlling movement of a catheter that is at least partially disposed therein a urinary catheter pouch, comprising:
   a) a catheter housing having a longitudinal axis and defining a longitudinally extending catheter tube pathway configured for receipt of the catheter, wherein the catheter tube pathway comprises an egress end and an ingress end; and
   b) a means for selectively engaging the catheter to permit longitudinal movement of the catheter relative to the catheter tube pathway in a first direction and to resist longitudinal movement of the catheter relative to the catheter tube pathway in a second, opposite direction, wherein the means for selectively engaging the catheter comprises:
      i) a leveling surface positioned within the catheter tube pathway of the catheter housing proximate the egress end of the catheter tube pathway, wherein the leveling surface is positioned substantially normal to the longitudinal axis of the catheter housing;
      ii) a biasing surface positioned within the catheter tube pathway of the catheter housing at an acute angle with respect to the leveling surface, wherein the biasing surface is spaced from the leveling surface, and wherein the biasing surface and leveling surfaces define an interior cavity within the catheter tube pathway of the catheter housing; and
      iii) a tube gripper positioned within the interior cavity of the catheter housing, the tube gripper having a top face, a bottom face, and defining a catheter orifice extending between the top face and the bottom face, wherein the catheter orifice comprises a gripping surface configured to frictionally engage an exterior surface of the catheter; and wherein movement of the catheter in a first direction moves the tube gripper into a first position, in which at least a portion of the top face of the tube gripper is in contact with the leveling surface such that the catheter orifice of the tube gripper is positioned substantially co-axial to the axis of the catheter tube pathway, and movement of the catheter in a second direction moves the tube gripper into a second position, in which the top face of the tube gripper is spaced therefrom the leveling surface and at least a portion of the bottom face of the tube gripper is in contact with the biasing surface such that the catheter orifice is positioned at an acute angle with respect to the axis of the catheter tube pathway.

2. The device of claim 1, wherein the egress end is positioned external of a urinary catheter pouch and the ingress end is contained within an interior volume of the urinary catheter pouch.

3. The device of claim 2, wherein the first direction is the longitudinal direction extending toward the egress end of the housing from the ingress end of the housing.

4. The device of claim 1, wherein the tube gripper is configured such that, upon the application of an external force on the catheter resulting in longitudinal movement of the catheter in the first direction, the tube gripper is positioned in the first position adjacent the leveling surface.

5. The device of claim 4, wherein the tube gripper is configured such that, upon the application of an external force on the catheter resulting in longitudinal movement of the catheter in the second direction, the tube gripper is positioned in the second position adjacent the biasing surface.

6. The device of claim 5, wherein, in the first position, the gripping surface of the tube gripper provides a first level of resistance to the movement of the catheter relative to the catheter tube pathway.

7. The device of claim 6, wherein, in the second position, the gripping surface of the tube gripper provides a second level of resistance to the movement of the catheter relative to the catheter tube pathway, wherein the second level of resistance is greater than the first level of resistance.

8. The device of claim 1, wherein the tube gripper is substantially ring shaped.

9. The device of claim 1, wherein the gripping surface comprises a plurality of gripping surfaces.

10. The device of claim 1, wherein the housing comprises a catheter introducer tip, and wherein the leveling surface is positioned within a portion of the catheter introducer tip.

11. The device of claim 1, wherein the tube gripper has a dimension extending from the top face to the bottom face of from about 1 mm to about 3 mm.

12. The device of claim 1, wherein the leveling surface and the biasing surface are spaced a distance approximately equal to, or greater than, the thickness of the tube gripper.

13. The device of claim 1, wherein the tube gripper has chamfered edges.

* * * * *